United States Patent
Satoda et al.

(10) Patent No.: US 8,327,903 B2
(45) Date of Patent: Dec. 11, 2012

(54) MANUFACTURING APPARATUS OF TRANSDERMAL ABSORPTION PREPARATION

(75) Inventors: Shiro Satoda, Ibaraki (JP); Shunetsu Kikuchi, Ibaraki (JP); Kazuhisa Ninomiya, Ibaraki (JP); Katsuhiro Okada, Ibaraki (JP); Hitoshi Akemi, Ibaraki (JP)

(73) Assignee: Nitto Denko Corporation, Osaka (JP)

( * ) Notice: Subject to any disclaimer, the term of this patent is extended or adjusted under 35 U.S.C. 154(b) by 49 days.

(21) Appl. No.: 12/000,742

(22) Filed: Dec. 17, 2007

(65) Prior Publication Data
US 2008/0149277 A1   Jun. 26, 2008

(30) Foreign Application Priority Data
Dec. 20, 2006 (JP) ................................. 2006-343395

(51) Int. Cl.
*B29C 43/30* (2006.01)
(52) U.S. Cl. ....................................... 156/548; 156/578
(58) Field of Classification Search .................. 156/289, 156/548, 549, 578; 118/686, 692
See application file for complete search history.

(56) References Cited

U.S. PATENT DOCUMENTS

| | | | |
|---|---|---|---|
| 4,655,768 A * | 4/1987 | Marecki et al. | 424/448 |
| 4,915,950 A | 4/1990 | Miranda et al. | |
| 5,603,953 A * | 2/1997 | Herbig et al. | 424/473 |
| 5,681,413 A | 10/1997 | Hille et al. | |
| 5,688,523 A * | 11/1997 | Garbe et al. | 424/448 |
| 5,958,447 A | 9/1999 | Haralambopoulos et al. | |
| 2003/0113356 A1 * | 6/2003 | Deckner et al. | 424/401 |
| 2004/0126415 A1 * | 7/2004 | Lu et al. | 424/449 |
| 2004/0247794 A1 * | 12/2004 | Tokimasa et al. | 427/421.1 |
| 2006/0078602 A1 * | 4/2006 | Kanios | 424/449 |
| 2007/0087043 A1 * | 4/2007 | Satoda et al. | 424/449 |

FOREIGN PATENT DOCUMENTS

| | | |
|---|---|---|
| EP | 1449527 A2 * | 8/2004 |
| EP | 1 749 521 | 2/2007 |
| EP | 1 774 964 | 4/2007 |
| JP | 11-502840 | 3/1999 |
| JP | 2004-195348 | 7/2004 |
| WO | 96/30001 | 10/1996 |

OTHER PUBLICATIONS

Definition of Band, Dictionary.com [online], [retrieved on Oct. 13, 2009], retrieved from [http://dictionary.reference.com/browse/band].*
European Search Report issued Feb. 23, 2011 in corresponding European Application No. 07 25 4783.
An Official Decision of Grant issued May 3, 2011 in corresponding Russian Application No. 2007147360.

* cited by examiner

*Primary Examiner* — Matthew Daniels
*Assistant Examiner* — Yana Belyaev
(74) *Attorney, Agent, or Firm* — Wenderoth, Lind & Ponack, L.L.P.

(57) ABSTRACT

A manufacturing apparatus of a transdermal absorption preparation includes an adhesive sheet supplying part to feed out a band-like first adhesive sheet into a runway, wherein the adhesive sheet has at least an adhesive layer comprising an adhesive and a liquid component compatible with the adhesive, a drug liquid application part to apply a given amount of a drug liquid to an adhesive face, and a traveling section for impregnation which is set in the runway after the drug liquid application part, during which the adhesive sheet is run for a period necessary for the applied drug liquid to soak into the adhesive layer without contact of the drug liquid coated face of the adhesive layer with other members.

10 Claims, 3 Drawing Sheets

(a)

(b)

(a)

(b)

MANUFACTURING APPARATUS OF TRANSDERMAL ABSORPTION PREPARATION

FIELD OF THE INVENTION

The present invention relates to a manufacturing apparatus for transdermal absorption preparation, and particularly relates to an apparatus capable of preferably impregnating an adhesive layer of an adhesive sheet with a pharmaceutical agent.

BACKGROUND OF THE INVENTION

Transdermal absorption preparation is generally produced by laminating an adhesive layer containing a drug on a substantially drug-impermeable support. Such transdermal absorption preparation is generally produced by applying a solution of an adhesive containing a drug in an organic solvent to the aforementioned support, drying the adhesive layer with hot air etc. to evaporate the organic solvent in the adhesive solution and, when desired, crosslinking the adhesive and the like.

When a drug is contained in an adhesive solution, however, since an undesirable phenomenon due to an interaction of the drug and the adhesive layer component may be developed, depending on the combination of the drug and the adhesive layer component, the decision of the formulation requires consideration that consumes time and expense. In addition, when an adhesive layer is subjected to a crosslinking treatment, since undesirable phenomenon such as crosslinking failure, denaturation of drug and the like due to an interaction of a certain kind of crosslinking agent and the drug can occur, the decision of the formulation requires consideration that consumes time and expense.

To remove such possibilities, a production method including applying an adhesive solution to a support and drying the same to give an adhesive sheet free of a drug (hereinafter sometimes to be referred to as "placebo"), applying, when desired, a crosslinking treatment, coating the surface of an adhesive layer with a drug liquid (i.e., liquid drug and/or drug solution), and allowing the drug to soak into the adhesive layer is advantageous.

JP-A-H11-502840 discloses a method for continuously manufacturing a pressure sensitive skin adhesive sheet material containing a liquid by combining a coating vehicle containing the liquid and a polymer base layer.

However, the production method disclosed in this publication does not disclose that a liquid component is contained in a pressure sensitive skin adhesive. Therefore, efficient impregnation of a pressure sensitive skin adhesive with a liquid pharmaceutical agent may be difficult. In addition, since this publication is directed to a coating vehicle containing a liquid rather than a pressure sensitive skin adhesive, this publication dissuades those of ordinary skill in the art to add a liquid component to an adhesive layer.

Moreover, this publication does not specifically disclose a method of impregnating a base layer with a pharmaceutical agent with regard to the manufacturing apparatus disclosed therein, let alone suggesting the time up to the impregnation of the adhesive layer with the coated drug solution, and an adhesive sheet traveling section for impregnation.

As mentioned above, the conventional techniques do not disclose or suggest an apparatus capable of producing a transdermal absorption preparation conveniently and efficiently, while avoiding disadvantages caused by the addition of a drug to an adhesive solution in the production of a transdermal absorption preparation.

SUMMARY OF THE INVENTION

An object of the present invention is to provide a manufacturing apparatus capable of producing a transdermal absorption preparation with less physical skin irritation on peeling, and improved feeling during adhesion by directly applying a drug liquid, namely, a liquid drug and/or a drug solution to an adhesive layer.

Intensive studies have been conducted in an attempt to solve the above-mentioned problems and found that the object transdermal absorption preparation can be obtained by only constituting an adhesive layer of an adhesive sheet to be a base for constituting a transdermal absorption preparation with an adhesive and a liquid component, selecting such a combination of a drug liquid, an adhesive and a liquid component allowing impregnation of the adhesive layer with the drug liquid, and setting a given distance of a section for the adhesive sheet to travel after application of the drug liquid to an adhesive face of the adhesive sheet, which resulted in the completion of the present invention.

Accordingly, the present invention is characterized by the following.

(1) A manufacturing apparatus of a transdermal absorption preparation, comprising an adhesive sheet supplying part to feed out a band-like first adhesive sheet into a runway, wherein the adhesive sheet has at least an adhesive layer comprising an adhesive and a liquid component compatible with the adhesive, a drug liquid application part to apply a given amount of a drug liquid, which is a liquid drug and/or a drug solution, to an adhesive face of the traveling adhesive sheet, wherein the combination of the drug liquid, an adhesive and the liquid component is so determined as to allow impregnation of the adhesive layer with the drug liquid, and a traveling section for impregnation which is set in the runway after the drug liquid application part, during which the adhesive sheet is run for a period necessary for the applied drug liquid to soak into the adhesive layer.

(2) The apparatus of the above-mentioned (1), wherein the combination of the drug liquid, the adhesive and the liquid component is so determined as to achieve a contact angle of the drug liquid with the adhesive face of 20 degrees-60 degrees.

(3) The apparatus of the above-mentioned (1) or (2), wherein the drug liquid is a drug solution or a liquid drug.

(4) The apparatus of any one of the above-mentioned (1) to (3), wherein the drug liquid application part is constituted to discharge a given amount of a drug liquid on the adhesive face from a delivery headset closer to the adhesive face.

(5) The apparatus of the above-mentioned (4), wherein the shape of an outlet opening of the delivery head is a slot covering not less than half of the whole width of the adhesive face so that the drug liquid will be discharged over the region covering not less than half of the whole width of the adhesive face.

(6) The apparatus of the above-mentioned (4) or (5), wherein the runway comprises a roll in contact with the back face of the adhesive sheet, the roll has a horizontal rotation shaft, the runway is constituted in such a manner that the adhesive face of the adhesive sheet will rotate from the downward to the upward for 180 degrees along the roll, and a delivery head is set within the range of −90 degrees-+90 degrees about the middle point between the lowermost point and the uppermost point of the roll.

(7) The apparatus of any one of the above-mentioned (4) to (6), wherein the delivery head is so directed as to set an angle θ1 formed by the adhesive face and the drug liquid discharge direction to 80-110 degrees as measured at the downstream of the delivery head.

(8) The apparatus of any one of the above-mentioned (1) to (7), which further comprises, after the traveling section for impregnation in the runway, a release liner laminating part for adhering a band-like release liner to an adhesive face of the traveling adhesive sheet.

(9) The apparatus of any one of the above-mentioned (1) to (8), wherein the runway further comprises, after the traveling section for impregnation, a second adhesive sheet supplying part for supplying a band-like second adhesive sheet, which has a constitution for adhering an adhesive face of the second adhesive sheet to an adhesive face of the first adhesive sheet.

BRIEF DESCRIPTION OF THE DRAWINGS

FIG. 2(a) is a sectional view of a delivery head when seen from the side. FIG. 2(b) schematically shows differentiation of a discharged drug liquid from a layer state to a water drop state.

Each symbol in the Figures shows the following. A; adhesive sheet supplying part, B; drug liquid application part, C; traveling section for impregnation, D; release liner supplying part, E; release liner laminating part, F; product receipt part, 1; support sheet, 2; adhesive layer, 3; adhesive sheet, 4; drug liquid, 5; release liner.

DETAILED DESCRIPTION OF THE INVENTION

The manufacturing apparatus of the present invention specifically has a traveling section for impregnation, which enables a drug liquid, which is applied to an adhesive sheet by a drug liquid application part, to soak into the adhesive sheet during traveling of the adhesive sheet for a given length of a runway. Since the adhesive layer contains a liquid component, the drug liquid can completely soak into the adhesive layer during the short time when the adhesive sheet travels the runway. In addition, since the traveling section for impregnation is formed in such a manner that the adhesive sheet can travel without contact of the drug liquid coated face of the adhesive layer with other members, the drug liquid soaks into the adhesive sheet substantially uniformly. Accordingly, the manufacturing apparatus of the present invention is particularly suitable for continuously and efficiently producing transdermal absorption preparations by impregnating an adhesive sheet containing a liquid component with a drug liquid.

In addition, what cannot be predicted even by those of ordinary skill in the art in the field of production of an adhesive sheet is that, even when a drug liquid in the form of a droplet is applied to an adhesive sheet by a drug liquid application part, the drug liquid soaks into an adhesive sheet during travel of the adhesive sheet on the runway, and a transdermal absorption preparation containing a drug to practically harmless uniformity can be manufactured according to the manufacturing apparatus of the present invention.

Figure 1:
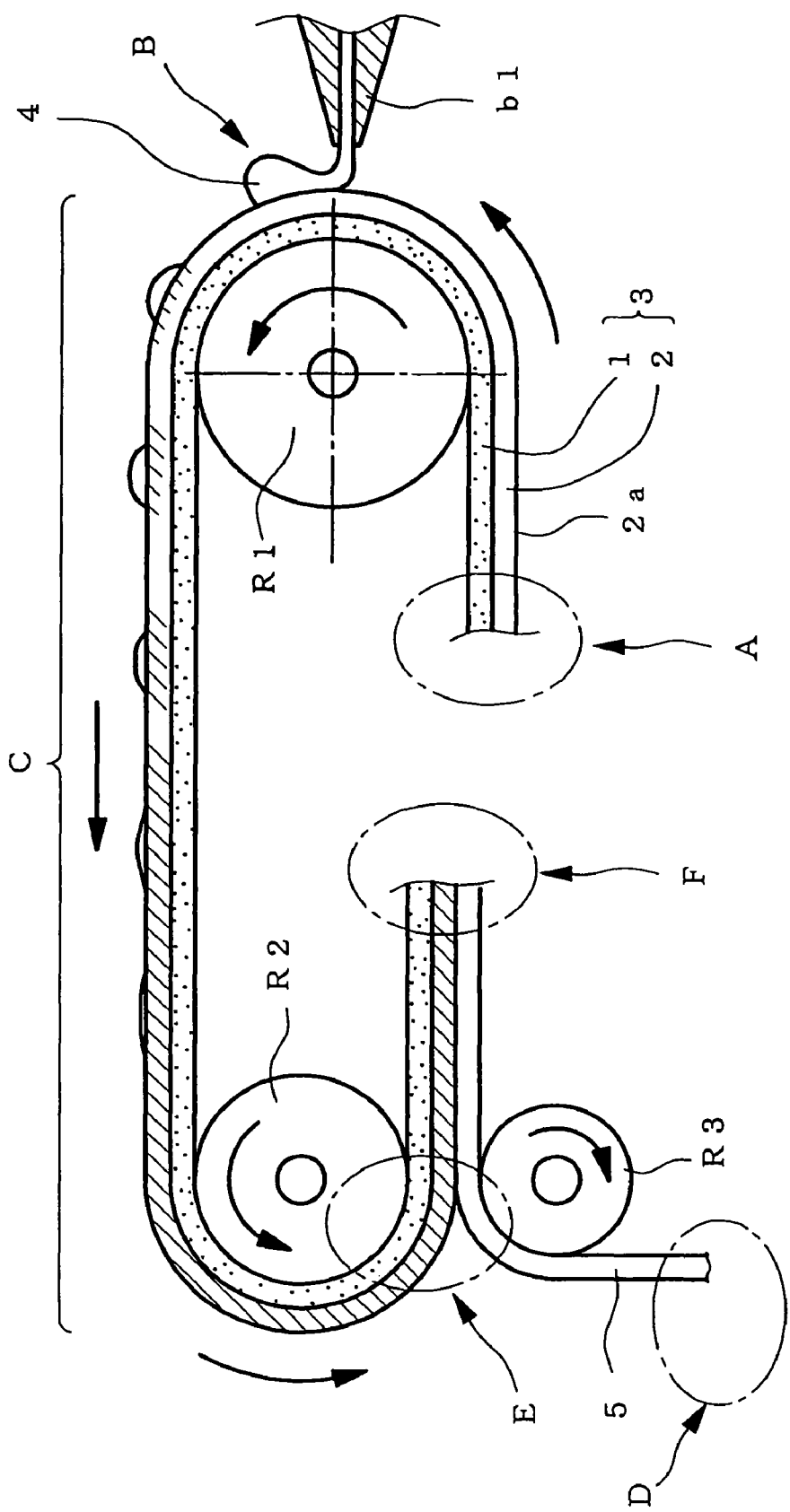
FIG. 1 schematically shows only the main part of the manufacturing apparatus of the present invention.

FIG. 1 schematically shows only the main part of the manufacturing apparatus of the present invention (the apparatus). While the adhesive sheet in the Figure is a laminate, the thickness of each layer is drawn in an exaggerated manner for easy understanding of the action effect.

As shown in the Figures, the apparatus has an adhesive sheet supplying part (A) to feed out a band-like first adhesive sheet 3 to the runway. In the following, the "band-like first adhesive sheet" is explained by simply referring to "an adhesive sheet" except when it needs to be distinguished from the below-mentioned "second adhesive sheet".

In the present invention, the adhesive sheet has a long band-like shape with the original width before cutting into a sheet-like product for continuous production and processing of sheet-like products, which travels in the longitudinal direction.

The detailed mechanism of the sheet supplying part itself is not shown. The runway is a passage pathway of an adhesive sheet, which consists of a roll, a guide plate and the like.

An adhesive sheet 3 comprises at least an adhesive layer 2, and the adhesive layer 2 further comprises an adhesive and a liquid component, wherein the liquid component is compatible with the adhesive. The details of the adhesive and each material of the liquid component are mentioned below. A preferable embodiment of the adhesive sheet includes a laminate of a support sheet 1 and an adhesive layer 2, as shown in FIG. 1.

The present apparatus comprises a drug liquid application part (B) for application of a given amount of a drug liquid 4 to an adhesive face 2a of a traveling adhesive sheet 3 (i.e., of the both main surfaces of the adhesive layer 2; an exposed surface to which a drug is applied).

Here, the relationship between [a drug liquid to be applied to drug liquid application part (B)] and [an adhesive to be contained in an adhesive layer of the adhesive sheet, a liquid component] is important for the constitution of the apparatus. In the present invention, the drug liquid applied in the drug liquid application part (B) needs to soak or transfer into an adhesive layer comparatively rapidly, without being left on the adhesive face as a sole liquid, thereby forming an impregnation state. In the present invention, therefore, [a drug liquid] and [an adhesive contained in an adhesive layer, liquid component] are selected in advance in the relationship wherein, as mentioned above, after application of the drug liquid to the adhesive face, the drug liquid rapidly soaks into the adhesive layer to give a transdermal absorption preparation. Specific examples and combination of respective materials and preferable application method of a drug liquid are mentioned below.

According to the combination of [a drug liquid] and [an adhesive contained in an adhesive layer, liquid component] selected as mentioned above, the apparatus has a traveling section (C) for impregnation, which is formed after the drug liquid application part in the runway. In the traveling section (C) for impregnation, an adhesive sheet travels free of contact of a drug liquid application surface (adhesive face coated with a drug liquid) of the adhesive layer with other members at least for a period up to complete soaking of the applied drug liquid into the adhesive layer.

The "period up to complete soaking of the applied drug liquid into the adhesive layer" means not only the minimum time necessary for the applied drug liquid to completely soak into the adhesive layer, but also a redundant time as necessary.

The "other members" in the aforementioned travel of the adhesive sheet, which is free of a contact of a drug liquid application surface of the adhesive layer with other members, means a member adversely influencing soaking of a drug liquid into an adhesive layer upon contact with the adhesive face, such as a roll or guide plate formed in contact with an adhesive face to change the advancing direction of the adhesive sheet, a release liner to be adhered to give a product, and the like. In FIG. 1, after traveling through section (C) for impregnation, another member to be in first contact with the adhesive face is a release liner 5 to be placed on an adhesive face in the below-mentioned release liner laminating part (E).

In a conventional manufacturing apparatus of an adhesive sheet, an adhesive solution containing a drug, an organic solvent and the like are applied to a band-like support, a release liner and the like, and the coated adhesive sheet is evaporated to remove an organic solvent and the like in the adhesive solution with a hot air and the like derived from a drying means such as a dryer and the like formed in the runway immediately after coating.

Accordingly, even if removal of a liquid component from an adhesive layer is suggested in such a conventional apparatus, impregnation with a liquid component is not suggested. Needless to say, a traveling section for impregnation, which is unique to the present invention, where the adhesive sheet can travel for a given time up to complete soaking of the coated drug liquid into an adhesive layer, is not suggested in conventional apparatuses.

According to the manufacturing apparatus of an adhesive sheet of the present invention, an adhesive layer can be voluntarily impregnated with a drug liquid by merely traveling the adhesive sheet through such traveling section, without setting the adhesive sheet as a target of a drying means.

According to the manufacturing apparatus of the present invention, therefore, since the drug in an adhesive layer and the adhesive layer are not placed, after application of an adhesive solution to a band-like support, a release liner and the like, under severe conditions due to heat, air pressure and the like derived from a drying means, an adverse influence on the adhesive layer is reduced. Specifically, conventional defects caused by dispersion, scattering or heat denaturation of the drug can be suppressed in the present invention.

In the present invention, since a traveling section (C) for impregnation is formed, a drug liquid applied to an adhesive face to swell up therefrom can naturally soak into the adhesive layer without an interfering contact with other members at least during passage of this section, whereby a uniform and preferable transdermal absorption and preparation can be achieved.

Prior to explanation of detailed embodiments of drug liquid application part (B) and traveling section (C) for impregnation, and embodiments of a drug liquid, an adhesive and liquid component contained in an adhesive layer, and a percutaneous absorber to be the production object, which are preconditions for determining the preferable embodiments, are now explained.

The drug liquid in the present invention includes a liquid drug, which is a drug in a liquid state, a drug solution wherein a drug is dissolved in any liquid, a drug dispersion wherein fine drug particles are substantially uniformly dispersed in any liquid and a mixture thereof. Since a production step is convenient, a drug solution or a liquid drug is preferable as a drug liquid, and a liquid drug is more preferable.

Examples of the aforementioned liquid include organic compound and/or inorganic compound and the like, which may be a combination of one or more kinds thereof. In view of the compatibility with a drug and compatibility with an adhesive, such liquid is preferably an organic compound. Examples of the liquid organic compound include fatty acid alkyl ester, alcohol and the like. Examples of the specific organic compound material include liquid organic compounds to be recited later as examples of the liquid component materials to be contained in an adhesive layer. A liquid can be selected therefrom independently of the substance to be used for the liquid component.

For efficient soaking of a drug liquid in an adhesive layer, the liquid to be contained in a drug liquid and the liquid component to be contained in an adhesive layer are preferably of the same kind. In addition, the drug solution may contain a thickener, a polymer resin and the like.

The drug concentration of a drug liquid is not particularly limited as long as the drug is contained in a proportion of more than 0 wt % and a drug liquid is a liquid. When a drug solution or a drug dispersion is used, the concentration of the drug is less than 100 wt % and, when a liquid drug is used, a liquid drug is used as a drug liquid without dilution with a solvent. In other words, since a drug liquid may be a drug per se, the drug concentration of a drug liquid is not more than 100 wt %.

The drug is not particularly limited, and a drug that can be administered to a mammal through the skin, namely, a transdermally absorptive drug, is preferable. Specific examples of such drug include general anesthetic drug, hypnotic sedative drug, antiepileptic drug, anti-pyretic and anti-inflammatory analgesic drug, seasick remedy, psychoneurotic drug, skeleton muscle relaxant, autonomic nervous system drug, spasmolytic drug, antiparkinsonian drug, antihistamine drug, cardiac stimulant, antiarrhythmic drug, diuretic drug, hypotensive drug, vasoconstrictor, coronary vasodilator, peripheral vasodilator, anti-arteriosclerotic drug, cardiovascular drug, respiratory stimulant, antitussive and expectorant drug, hormonal drug, external medicine for purulent disease, analgesic•antipruritic•astringent•anti-inflammatory drug, drug for parasitic dermatic disease, haemostatic drug, gout remedy, diabetes drug, antineoplastic drug, antibiotic, chemotherapeutic drug, narcotic drug, antidepressant drug, stop smoking aid and the like.

The liquid drug mentioned here means a drug which shows flowability at room temperature, or at 25° C., namely, a drug whose viscosity is 0.05-100,000 mPa·s. Examples of the liquid drug include emedastine, crotamiton, gallopamil, nitroglycerin, terbinafine, oxybutynin, β-blocker, nicotine and a derivative thereof and the like. In view of efficient production of a transdermal absorption preparation, a drug liquid which rapidly soaks in an adhesive layer is preferable, and examples of such drug liquid include nicotine.

While a viscosity of the drug liquid is not particularly limited, in view of easy application, 0.05-100000 mPa·s is preferable. The viscosity of a liquid drug or a drug liquid mentioned here is measured with an E type viscometer while keeping the temperature of a sample of the drug liquid at 25° C.

While an amount of the drug which soaks in an adhesive layer can be appropriately determined depending on an administration object, the drug is preferably contained in a proportion of about 1-40 wt %, more preferably 1-20 wt %, most preferably 5-20 wt %, of an adhesive layer. When it is less than 1 wt %, the treatment effect may become insufficient, and when it exceeds 40 wt %, skin irritation may be developed, which may lead to an economical disadvantage.

When a drug liquid shows a particular contact angle, namely, 90-180 degrees, and the drug liquid is directly applied to a general adhesive layer, the drug liquid is repelled by the adhesive layer and does not immediately soak in the adhesive layer, which may impair efficient production of a transdermal absorption preparation for transdermal absorption of the drug liquid.

Therefore, as mentioned below, a liquid component suitable for impregnation with the drug liquid is added to the adhesive layer, whereby a transdermal absorption preparation can be efficiently produced using the manufacturing apparatus of the present invention.

Since an adhesive layer contains a large amount of liquid component, a preferable dosage form of a transdermal absorption preparation to be produced by the apparatus is preferably a laminate wherein the adhesive layer is formed on a support sheet. Further, as an embodiment of the product, it is preferable that an adhesive face of the adhesive layer be covered with a release liner.

When the final form of the preparation is a laminate such as the one mentioned above, the adhesive sheet to be fed in the apparatus from an adhesive sheet supplying part to a runway may be a laminate wherein an adhesive layer is formed on a support sheet, or, conversely, may be a laminate wherein an adhesive layer is formed on a release liner. Either of the embodiments may be employed as long as a drug can be applied to the surface of an adhesive layer of the laminate.

When a laminate wherein an adhesive layer is formed on a release liner is supplied, of the both main surfaces of the adhesive layer, a support sheet is placed on an adhesive face applied with a drug, and when used, an adhesive face of the release liner side is the face which contacts a living organism. Other layers may exist between the support sheet and the adhesive layer, as necessary.

An adhesive sheet supplying part (A) of the apparatus may be provided with a necessary mechanism for feeding an adhesive sheet to a runway, such as an apparatus that maintains a material roll comprising a wound adhesive sheet, rewinds and feeds the material roll, an apparatus for separating the release liner and winding it at that time, and the like. Such mechanism may be a different apparatus that cooperates outside the apparatus. In that case, the adhesive sheet supplying part of the apparatus is a mere receiving entrance or an apparatus for receiving the adhesive sheet sent from outside the apparatus and discharging the adhesive sheet to a runway, and the like. The adhesive sheet supplying part of the apparatus may be any as long as it is so constituted as to feed an adhesive sheet to a runway.

While as an adhesive which is a constitution component of the adhesive layer, an adhesive generally used in the field of transdermal absorption preparation, such as rubber adhesive, vinyl adhesive, acrylic adhesive and the like, can be used, and an adhesive having properties enabling crosslinking treatment is preferable.

Examples of the rubber adhesive include adhesives containing silicone rubber, polyisoprene rubber, polyisobutylene rubber, styrene-butadiene rubber, styrene-isoprene-styrene block copolymer rubber, styrene-butadiene-styrene block copolymer rubber and the like as a main component.

Examples of the vinyl adhesive include adhesives containing polyvinyl alcohol, polyvinyl alkyl ether, polyvinyl acetate and the like as a main component.

While the acrylic adhesive is not particularly limited, a copolymer wherein alkyl (meth)acrylate is copolymerized as a main component is preferable since a crosslinking treatment is easily performed. As the alkyl (meth)acrylate, an alkyl (meth)acrylate wherein the alkyl moiety is linear, branched chain or cyclic alkyl group having 4 to 18 carbon atoms (e.g., butyl, pentyl, hexyl, heptyl, octyl, nonyl, decyl, undecyl, dodecyl, tridecyl, 2-ethylhexyl, cyclohexyl etc.) is preferable. One or more kinds of these alkyl (meth)acrylates can be used in combination. Of these, a monomer that decreases the glass transition temperature is preferable to afford adhesiveness at ambient temperature, and an alkyl (meth)acrylate wherein the alkyl moiety is linear, branched chain or cyclic alkyl group having 4 to 8 carbon atoms (e.g., butyl, pentyl, hexyl, heptyl, octyl, 2-ethylhexyl, cyclohexyl etc., preferably butyl, 2-ethylhexyl or cyclohexyl, particularly preferably 2-ethylhexyl) is more preferable. Examples of the alkyl (meth)acrylate wherein the alkyl group has 4 to 8 carbon atoms include butyl acrylate, 2-ethylhexyl acrylate, 2-ethylhexyl methacrylate, cyclohexyl acrylate and cyclohexyl methacrylate are preferable, and 2-ethylhexyl acrylate is most preferable.

In addition, as a second component to be copolymerized with the above-mentioned monomer, a monomer having a functional group that can be a crosslinking point when using a crosslinking agent may be used. In the present invention, vinyl monomer containing a hydroxyl group or a carboxyl group as a functional group is preferably used. As the second component monomer, for example, hydroxyethyl (meth)acrylate (e.g., 2-hydroxyethyl acrylate), hydroxypropyl (meth)acrylate, (meth)acrylic acid, itaconic acid, maleic acid, mesaconic acid, citraconic acid, glutaconic acid and the like can be used. One or more kinds of these second monomer components can be used in combination.

A third monomer component may be copolymerized besides the above-mentioned second monomer component. The component is used for controlling the cohesion of the adhesive layer or controlling the solubility and release performance of a drug liquid. Examples of the third monomer component include vinyl esters such as vinyl acetate, vinyl propionate and the like, vinyl ethers such as methyl vinyl ether, ethyl vinyl ether and the like, vinylamides such as N-vinyl-2-pyrrolidone, N-vinylcaprolactam and the like, alkyl (meth)acrylates, hydroxyl group-containing monomers such as hydroxypropyl (meth)acrylate, α-hydroxymethyl acrylate and the like, amide group-containing monomers such as (meth)acrylamide, dimethyl(meth)acrylamide and the like, alkoxyl group-containing monomers such as methoxyethyl (meth)acrylate, ethoxyethyl (meth)acrylate and the like, vinyl monomers such as styrene, vinylpyridine, vinylimidazole, vinylmorpholine and the like, and the like. One or more kinds of these third monomer components can be used in combination.

In the present invention, when using a copolymer of the above-mentioned alkyl (meth)acrylate and the above-mentioned second monomer component as an acrylic adhesive, while there is no particular limitation, for example, copolymerization may be carried out by mixing at a weight ratio of alkyl (meth)acrylate:second monomer=about 40-99.9:0.1-10.

Moreover, when using the above-mentioned third monomer component, while there is no particular limitation, for example, copolymerization may be carried out by mixing at a weight ratio of alkyl (meth)acrylate:second monomer:third monomer=about 40-99.9:0.1-10:0-50.

The polymerization reaction can be carried out by a method known per se, and examples include a method wherein the above-mentioned monomers were added with a polymerization initiator (e.g., benzoyl peroxide, 2,2'-azobisisobutyronitrile etc.), and reacted in a solvent (ethyl acetate etc.) at 50-70° C. for 5-48 hr.

Of the above-mentioned adhesives, silicone rubber and acrylic adhesive are preferable adhesives from an aspect that a crosslinking treatment can be easily carried out using a crosslinking agent. Particularly, from an aspect that a drug liquid can easily soak in an adhesive layer when the below-mentioned liquid component is contained, an acrylic adhesive is preferable.

In the present invention, a liquid component compatible with the above-mentioned adhesive is contained in an adhesive layer.

The [liquid component compatible with an adhesive] includes not only chemical dissolution but also substantially uniform dispersion.

In the present invention, since an adhesive sheet contains a liquid component, shedding of a drug liquid on an adhesive surface during application of the liquid can be suppressed. Thus, is the drug liquid can be applied uniformly and quickly soaks into the adhesive sheet. Consequently, it is possible to directly apply a drug liquid to an adhesive layer, and continuously produce transdermal absorption preparations while maintaining highly precise content uniformity.

In addition, the liquid component plasticizes an adhesive to impart a soft feeling, and is effective for reducing pain and skin irritation due to adhesion to the skin, when peeling off a percutaneous absorber from the skin.

Moreover, a liquid component adjusts the contact angle of a drug liquid relative to an adhesive layer free of application of a drug (i.e., before application of a drug liquid) to 20-60° and the like suitable for soaking.

Accordingly, the liquid component may be any as long as it enables production of a transdermal absorption preparation by, for example, plasticizing an adhesive, adjusting a contact angle of a drug liquid relative to an adhesive layer, improving an absorption speed of an adhesive layer, and the like. When plural drugs are used simultaneously, a drug having an absorption promoting action to improve transdermal absorbability can also be used.

As the liquid component, an organic compound is preferable from the aspect of compatibility with an adhesive. Examples thereof include fats and oils such as olive oil, castor oil, squalene, lanolin and the like, organic solvents such as dimethyldecyl sulfoxide, methyloctyl sulfoxide, dimethyl sulfoxide, dimethylformamide, dimethylacetamide, dimethyllaurylamide, methylpyrrolidone, dodecylpyrrolidone and the like, liquid surfactants, plasticizers such as diisopropyl adipate, phthalic acid (di)esters (e.g., diisononyl phthalate, di(2-ethylhexyl)phthalate etc.), diethyl sebacate and the like, hydrocarbons such as liquid paraffin and the like, fatty acid alkyl esters (e.g., ester of alcohol wherein the alkyl moiety is linear, branched chain or cyclic alkyl having 1 to 13 carbon atoms and saturated or unsaturated fatty acid having 8 to 18 carbon atoms, and the like, specifically, ethyl oleate, isopropyl palmitate, octyl palmitate, isopropyl myristate, isotridecyl myristate, ethyl laurate etc.), glycerol fatty acid esters (e.g., ester of glycerol and saturated or unsaturated fatty acid having 8 to 16 carbon atoms, and, the like, specifically, tri(caprylic acid/capric acid)glyceride, and the like), propylene glycol fatty acid esters (e.g., ester of propylene glycol and saturated or unsaturated fatty acid having 8 to 16 carbon atoms, and the like, specifically, propyleneglycol dicaprylate and the like), fatty acid esters such as alkyl pyrrolidonecarboxylate and the like, alkyl aliphatic dicarboxylates (e.g., ester of alcohol wherein the alkyl moiety is linear, branched chain or cyclic alkyl having 1 to 4 carbon atoms and saturated or unsaturated aliphatic dicarboxylic acid having 6 to 16 carbon atoms, and the like, specifically, diisopropyl adipate, diethyl sebacate and the like), higher alcohols such as octyldodecanol and the like, silicone oil, ethoxylated stearyl alcohol and the like. One or more kinds thereof can be used in a mixture. Of such liquid organic compounds, the above-mentioned fatty acid alkyl esters (e.g., isopropyl myristate, isopropyl palmitate and the like) and glycerol fatty acid esters (e.g., tri(caprylic acid/capric acid)glyceride, and the like) are preferable, and isopropyl myristate, isopropyl palmitate and glycerol fatty acid esters are particularly preferably used. Of glycerol fatty acid esters, tri(caprylic acid/capric acid)glyceride is particularly preferable.

In the present invention, the contact angle of a drug liquid relative to an adhesive layer free of a drug (i.e., before application of a drug liquid) is preferably adjusted to 20-60° by the above-mentioned liquid component. When the contact angle is greater than 60°, the applied drug liquid is repelled on the adhesive face and uniform application is not available. When the contact angle is smaller than 20°, a drug liquid flows on an adhesive sheet and uniform application is not available.

To reduce the contact angle to less than 20°, the ratio of the above-mentioned liquid component needs to be set to a very high level, which causes imbalanced adhesive property of adhesive force, cohesion, tack and the like, and easy development of peeling and adhesive residue. The contact angle is more preferably within the range of 25°-55°, most preferably within the range of 25°-50°.

As used herein, the "contact angle" refers to a contact angle obtained when 1.1 μL of a drug liquid droplet is brought into contact with the surface of an adhesive face, and the contact angle is measured 1 second later under the conditions of room temperature (23±2° C.), relative humidity (60±10% RH), unless particularly limited.

The contact angle of a drug liquid relative to an adhesive face is specifically measured as follows:

A sample is fixed on a slide glass with the adhesive face of an adhesive layer facing upward and the glass is mounted on a device. A drug liquid droplet (1.1 μL) is brought into contact with the adhesive face, and the contact angle is measured after 1 second under the above-mentioned conditions. Successively, the time course changes of the contact angle are measured every 9 seconds for up to 3 min.

In detail, the above-mentioned contact angle is measured using a contact angle measuring equipment (Model Drop-Master 700, manufactured by Kyowa Interface Science Co., Ltd).

The measurement function of the measurement apparatus is as follows: measurement range; contact angle 0-180°, measurement precision; contact angle ±1°, resolution: contact angle 0.1°, determination of measurement position: operation on PC display, given amount droplet preparation: automatic, liquid contact control/liquid contact recognition: automatic, contact angle analysis: automatic.

A (crosslinked) adhesive layer is fixed on a slide glass with the surface of a release liner facing upward and the glass is mounted on a device. The release liner is peeled off, a drug liquid droplet is brought into contact with the exposed adhesive face of an adhesive layer, and the contact angle is measured after 1 second under the conditions of room temperature 23±2° C., relative humidity 60±10% RH. The amount of the drug liquid droplet is adjusted to 1.1 μL.

When desired, the time course changes of the contact angle are successively measured every 9 seconds for up to 3 min.

For stable production of transdermal absorption preparations, a process of rapid absorption of the applied drug liquid into an adhesive layer is necessary and, in fact, absorption of a drug liquid by an adhesive layer is confirmed. Therefore, the contact angle of a drug liquid on an adhesive face is not stable, where the absorption of a drug liquid by an adhesive decreases the contact angle. When the decrease in the contact angle (rate of change) is high, stable production conditions can be afforded.

In the present invention, in the contact angle of a drug liquid relative to an adhesive as defined by the following formula, an adhesive layer showing a rate of change of the contact angle of not less than 15% at 1 second after dropwise addition of a drug liquid relative to a contact angle at 3 min after dropwise addition of a drug liquid is preferably used.

rate of change of contact angle={(amount of change in contact angle)/(contact angle 1 sec later)}×100 wherein (amount of change in contact angle)=(contact angle 3 min later)−(contact angle 1 sec later)

When a drug liquid is nicotine, it is preferable to adjust a penetration rate (soaking speed) of nicotine in an adhesive layer within the range of 0.3-6.7 mg/cm$^2$·min by appropriately adjusting the kind or amount of the liquid component.

When the penetration rate is not less than 0.3 mg/cm$^2$·min, a given amount of nicotine can soak in an adhesive layer at an appropriate traveling speed and at an appropriate traveling section for impregnation, which suppresses content dispersion of nicotine. When penetration rate is not more than 6.7 mg/cm$^2$·min, the ratio of the liquid component in an adhesive layer is within a preferable range, and adhesive properties such as adhesive force, coagulation power, tack and the like are well balanced, which suppresses detachment and adhesive residue.

When a drug liquid is nicotine, more preferable range of the penetration rate is 0.5-5.0 mg/cm$^2$·min, and the most preferable range is 0.8-3.8 mg/cm$^2$·min. In order to determine the penetration rate that falls within this range, the mixing ratio of an adhesive and liquid component in an adhesive layer is, in weight ratio, (1:0.25)-(1:1.8), in view of skin irritation, it is preferably (1:0.4)-(1:1.6). In other words, a liquid component is preferably contained in a large amount.

Particularly, when the drug liquid is nicotine, it is preferable to use fatty acid alkyl ester, particularly isopropyl myristate, glycerol fatty acid ester, more particularly tri(caprylic acid/capric acid)glyceride and the like as a liquid component, and set the mixing ratio of the adhesive and the liquid component in an adhesive layer to fall within the above-mentioned range. For achieving a particularly good balance between transdermal absorbability and adhesiveness, concomitant use of fatty acid alkyl ester and glycerol fatty acid ester is preferable. To easily realize the above-mentioned mixing ratio of the liquid components, a crosslinked acrylic adhesive is preferable.

A contact angle of a drug liquid with an adhesive is also reduced by partly mixing the same liquid component as the one added to the adhesive, with the drug liquid for application. This is a phenomenon found by the present inventors.

The larger the amount of the liquid component added is, the more the contact angle can be reduced. However, since a drug liquid is to be applied in a specified amount, when the amount of the liquid component is extremely large, the liquid needs to be applied unpreferably in a large amount. When the amount of the liquid component to be added is extremely small, the effect of reduction of the contact angle becomes small. Accordingly, the ratio of the liquid component to be added to a drug liquid is preferably 1-50 wt %, more preferably 5-30 wt %, still more preferably 10-20 wt %, relative to the whole mixture of the drug liquid and the liquid component.

While the thickness of an adhesive layer is not particularly limited, it is generally about 40-250 μm, preferably 50-240 μm, and from the aspects of skin adhesiveness and transdermal absorbability of a drug liquid, it is more preferably 66-200 μm, still more preferably 70-200 μm.

In order to provide appropriate coagulation power for application to the skin of a human and the like, it is preferable to perform a crosslinking treatment to an adhesive layer. Examples of a crosslinking treatment include chemical crosslinking treatment using crosslinking agent such as isocyanate compound (e.g., CORONATEHL (trade name, manufactured by Japan Polyethylene Corporation) and the like), metal chelate compound (metal chelate compound composed of, for example, titanium, zirconium, zinc or aluminum, specifically aluminum ethylacetoacetate·diisopropylate), organic peroxide, epoxy compound, melamine resin, metal alcoholate and the like, and physical crosslinking treatment using UV, γ ray, electron ray and the like. Of these, from the aspects of reactivity and handling, chemical crosslinking treatment using a crosslinking agent such as metal alcoholate composed of isocyanate compound, titanium, zirconium, zinc or aluminum, or metal chelate compound and the like is preferable. These crosslinking agents do not produce a thickening phenomenon of a solution before application and drying, thus, are extremely superior in workability.

A mixing amount of the crosslinking agent is about 0.01-5.0 parts by weight relative to 100 parts by weight of an adhesive. Within this range, an adhesive layer shows good balance between adhesive property of adhesive layer and adhesion to the skin, and the development of adhesive residue and skin irritation during peeling is suppressed.

Chemical crosslinking treatment may be carried out by a method known per se. Generally, the treatment can be carried out by adding a crosslinking agent and heating the mixture to a temperature not lower than the crosslinking reaction temperature. The heating temperature and the time may be appropriately selected depending on the kind of the crosslinking agent. Generally, the heating temperature is about 50-140° C. and the heating time is about for 1 day-1 week.

While the material or tissue of the support sheet is not particularly limited, one that does not permit passage and loss of the drug liquid impregnating the adhesive layer through the support sheet to cause content reduction. In other words, one made of a material impermeable to the drug liquid is preferable.

As a preferable support sheet, for example, a single film of polyester, nylon, saran, polyethylene, polypropylene, ethylene-vinyl acetate copolymer, poly(vinyl chloride), ethylene-ethyl acrylate copolymer, polytetrafluoroethylene, is metal foil, poly(ethylene terephthalate) and the like, and a laminate film of one or more kinds thereof and the like can be used.

Of these, in order to improve adhesiveness (anchor property) between a support sheet and an adhesive layer, it is preferable to make a support sheet of, for example, a laminate sheet of a non-porous sheet composed of the above-mentioned material and the following porous sheet, and form an adhesive layer on the porous sheet side. Such porous sheet is not particularly limited as long as it improves the anchor property between the support sheet and the adhesive layer. For example, a sheet subjected to a mechanical perforation treatment on paper, woven fabric, nonwoven fabric (e.g., poly(ethylene terephthalate) nonwoven fabric and the like), the above-mentioned film (e.g., a single film of polyester, nylon, saran, polyethylene, polypropylene, ethylene-vinyl acetate copolymer, poly(vinyl chloride), ethylene-ethyl acrylate copolymer, polytetrafluoroethylene, metal foil, poly(ethylene terephthalate) and the like, and a laminate film of one or more kinds thereof, and the like), and the like can be mentioned, and paper, woven fabric, nonwoven fabric (e.g., poly(ethylene terephthalate) nonwoven fabric and the like) are particularly preferable.

Considering the improvement of an anchor property and flexibility of the whole preparation, the thickness of the support sheet is preferably within the range of 10-500 μm. When woven fabric or nonwoven fabric is used as a porous sheet, the fabric weight amount is preferably 5-50 g/m², and from the aspects of the improvement of anchor property, the fabric weight amount is more preferably 8-40 g/m².

Examples of a laminate sheet made of a non-porous sheet and a porous sheet include a laminate sheet of a poly(ethylene terephthalate) film and poly(ethylene terephthalate) nonwoven fabric, and the like.

The above-mentioned contact angle of a drug liquid with an adhesive and the soaking rate into an adhesive layer are the same for drugs other than a drug liquid. The thickness of the adhesive layer, a crosslinking treatment of the adhesive layer, and the like can be appropriately selected to afford optimal values for each drug.

As a production method of an adhesive sheet to be supplied to the apparatus, the following embodiments can be mentioned.

(i) A mixed solution of an adhesive, a liquid component, and a crosslinking agent to be added as necessary is thoroughly stirred. The solution is applied to a support (or release liner) and dried to give a laminate having an adhesive layer. When this step is a different step independent of the apparatus, a release liner (or support) may be once placed on the adhesive layer. In addition, a crosslinking treatment such as heating and the like may be performed where necessary.

(ii) Then, an adhesive sheet with an exposed adhesive face to be applied with a drug is sent out from an adhesive sheet supply part to the runway. After passing a drug liquid application part and a traveling section for impregnation, a sheet such as a release liner, a support sheet and the like, which is necessary for completing a product, is appropriately layered thereon.

With the traveling adhesive sheet as a first adhesive sheet, a band-like second adhesive sheet is fed thereon and the first adhesive sheet and the second adhesive sheet may be adhered to each other in such a manner that the adhesive face of the first adhesive sheet is adhered to an adhesive face of the second adhesive sheet. This processing aims at thickening the adhesive layer. A simple application processing is insufficient to thicken an adhesive layer beyond a given level. However, by adhering two sheets to each other, an adhesive layer can be thickened easily.

A greater thickness of an adhesive layer means a greater total content of the drug because an adhesive layer of the second adhesive sheet contains a drug. Thus, a greater amount of the drug can be supplied for a longer time after adhesion.

In such production embodiment, a second adhesive sheet supplying part to supply a band-like second adhesive sheet is formed after a traveling section for impregnation in the runway, where a second adhesive sheet is adhered to a traveling first adhesive sheet, in the same manner as in adhesion of a release liner. In this production embodiment, either one of the support sheets can be used as a release sheet (release liner).

Moreover, the drug to be contained in an adhesive layer of the second adhesive sheet may be the same as or different from the composition of the drug contained in an adhesive layer of the first adhesive sheet.

As a method for directly applying a drug liquid to an adhesive face in a drug liquid application part, a printing process used in the printing field can be employed. For example, techniques such as gravure coater, flexo coater, calendar coater, spray coater, curtain coater, fountain coater, die coater, inkjet and the like can be mentioned. When viscosity needs to be adjusted in a printing method, an additive may be added as appropriate to the extent that transdermal absorbability and viscosity are not affected.

These methods can be applied to thin film coating that generally requires high precision. When drug content uniformity is requested as in the present invention, these methods are advantageously used. In addition, since a drug liquid is used as an application liquid in the present invention, the application method is preferably one that can achieve high application precision even with an application liquid having a low viscosity. Furthermore, since a drug liquid has extremely high toxicity, the application method is desirably one highly safe for production workers, which is desirably not an open system. In consideration of these points, a method using an ink jet printer with a die coater or a piezo system is particularly preferable because it is superior in the coating precision and can be easily converted to a closed system.

The constitution of the most preferable apparatus for applying a drug liquid in a drug liquid application part is, for example, a die coater. In a die coater, a drug liquid is supplied to a delivery head b1 which is called "die" using a metering pump (not shown) from a supply tank (not shown).

As shown in FIG. 1, an adhesive layer (containing a liquid component) 2 supported by a support sheet 1 (or a release liner) is constituted to pass through the clearance between a back-up roll R1 and a delivery head b1, and a drug liquid is quantitatively and uniformly discharged onto an adhesive face 2a from the delivery head b1 set closer to the adhesive face 2a.

Figure 2:
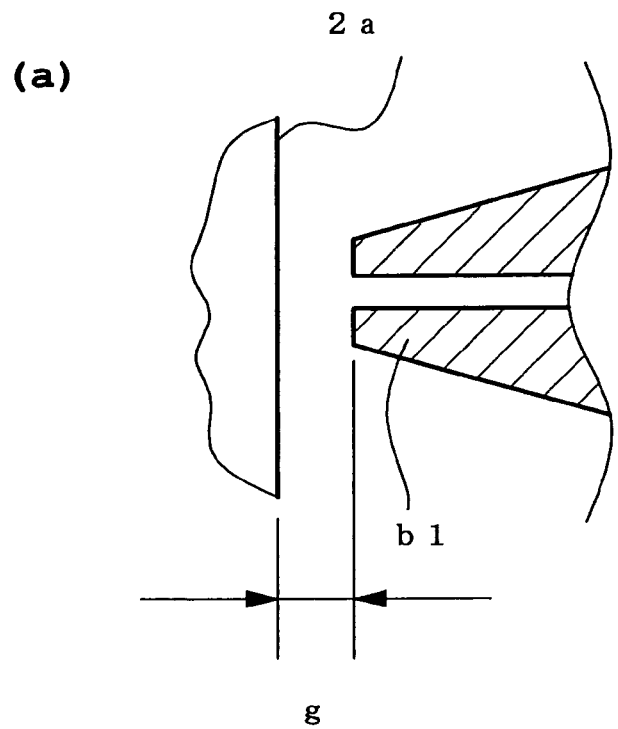
FIG. 2 is an enlarged view of a drug liquid application part of the manufacturing apparatus of the present invention.
Figure 2:
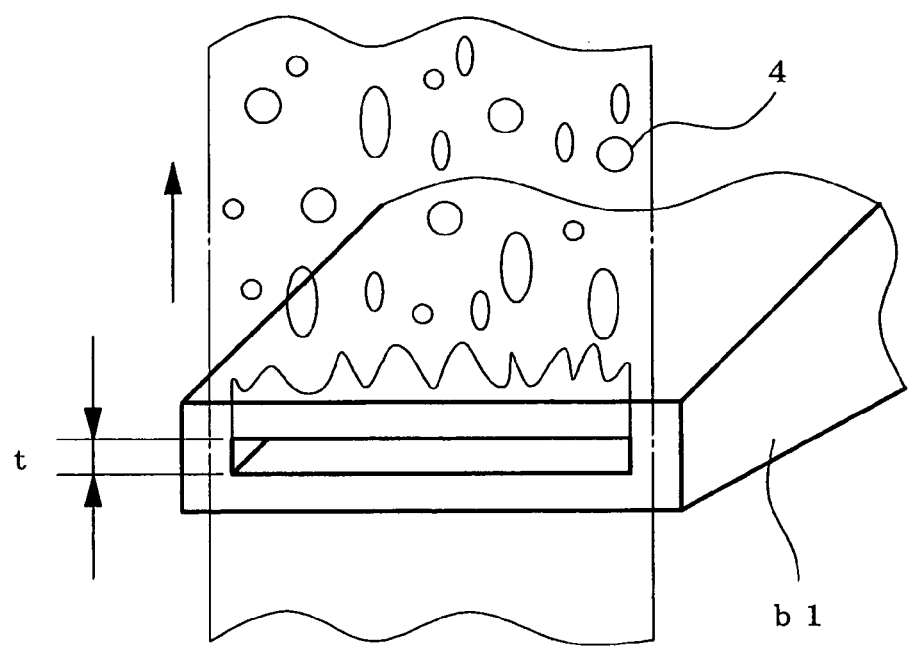

FIG. 1 schematically shows one embodiment wherein a drug liquid is discharged from the tip of a die, which is a delivery head b1, onto an adhesive face in a given amount. In the embodiment of FIG. 1, the drug liquid is continuously discharged. However, due to the relationship among a discharge amount, a feed amount of the adhesive sheet and the contact angle of the drug liquid with the adhesive face, the drug liquid is subdivided into water drops immediately after application, without continuously forming a liquid layer on the adhesive face. FIG. 1 schematically shows such process. FIG. 2(b) is a perspective view schematically showing subdivision of the drug liquid discharged from the tip of the die, from a layer state to a water drop.

Moreover, FIG. 1 schematically shows the drug liquid broken into small parts gradually soaking into the adhesive layer in the traveling section for impregnation. In this Figure, the drug liquid soaking into the adhesive layer is shown by hatching. Due to the relationship among a discharge amount, a feed amount of the adhesive sheet and the contact angle of the drug liquid with the adhesive face, the continuously discharged drug liquid may gradually soak into the adhesive layer in the traveling section for impregnation while forming a liquid layer on the adhesive face of the adhesive sheet.

Examples of the die, which is a delivery head of a die coater, include curtain die, ultra die, lip die, slot die and the like. Of these, a slot die whose shape of an outlet opening is like a slot capable of covering not less than half the width, preferably the whole width, so that a drug liquid can be discharged over not less than half the width, preferably the whole width, of the adhesive face, is preferable because a low viscosity solution can be applied with high precision.

The shape of the opening of the outlet opening of a slot die is, as shown in FIG. 2(b), a rectangle having a fine slot void (t) as a short side, and the delivery head is provided such that the direction of the long side of the rectangle will be the same as the width direction of the adhesive face.

The position of the delivery head is not particularly limited as long as the outlet opening is diagonal with an adhesive sheet. As shown in FIG. 1, a position such that roll R1 for changing the sheet advancing direction is in contact with the back face of an adhesive sheet (surface on the opposite side from the adhesive face) is preferable. When an adhesive sheet is backed up (backing) by roll R1, the surface of an adhesive layer is maintained smooth and the accurate amount of the drug liquid to be applied can be easily controlled.

As shown in FIG. 1, an adhesive sheet is applied for backing by a roll R1 having a horizontal rotation shaft. When the adhesive face 2a rotates for 180 degrees from the downward to the upward along the roll, the position of the delivery head is preferably within the range where the roll is present on the back of the adhesive sheet (i.e., in FIG. 3(b), the range of an adhesive sheet moving from the lowermost point to the uppermost point along the roll R1; in other words, within the range of ±90 degrees about the middle position m).

In this case, since the roll as a back-up is in close contact with the back face of the adhesive sheet, the clearance between the surface of the adhesive layer and the delivery head is stable, while the thickness of the adhesive sheet varies. Thus, the clearance can be controlled accurately and the production is stabilized.

Figure 3:
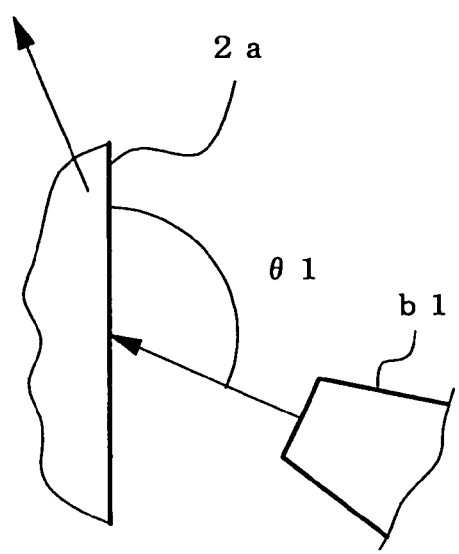
FIG. 3 shows a preferable embodiment of a drug liquid application part.
Figure 3:
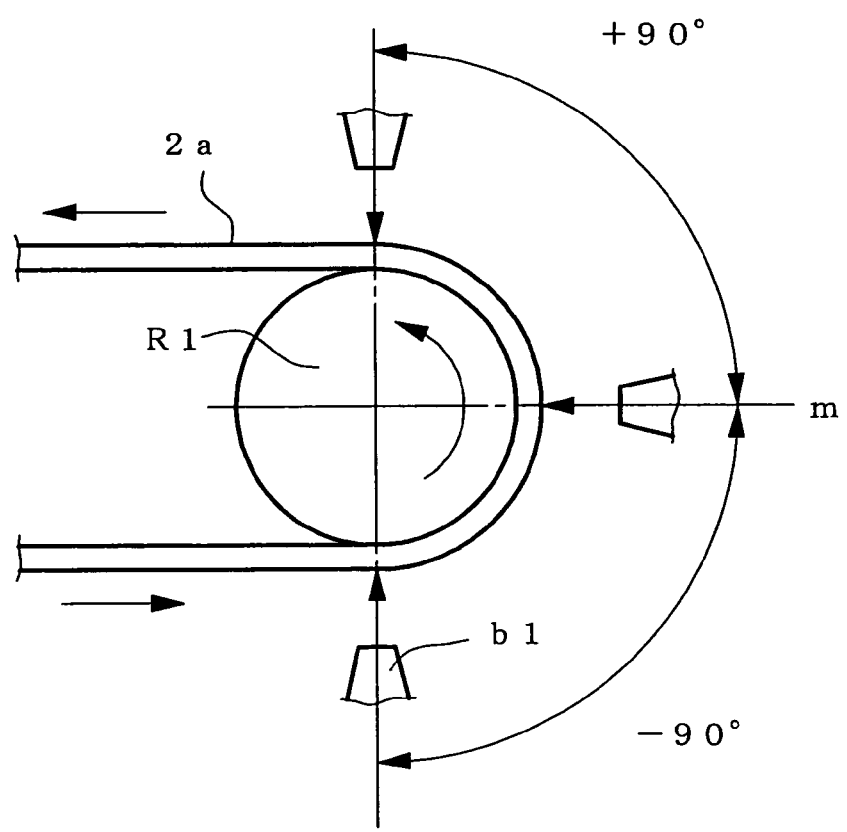

In the embodiment of FIG. 3(b), a more preferable range of the position of the delivery head is within the range of (−20 degrees)-(+80 degrees) about the middle point (m) between the lowermost point and the uppermost point of the movement of the adhesive sheet along the horizontal roll R1. Of the indicated range, ±20 degrees is preferable and ±10 degrees is particularly preferable; about the middle point m.

When the delivery head is set near the lowermost point of the horizontal roll, the drug liquid needs to be discharged approximately straight up, and the drug liquid may partly run down along the outer side of the delivery head. The drug liquid applied to the adhesive face may run down before soaking, making a non-uniform application of the drug liquid.

Furthermore, when the delivery head is set near the uppermost point of the horizontal roll, the drug liquid needs to be discharged approximately straight down. While the downward discharge does not greatly influence the applicability itself, the operator needs to peer into the outlet opening from the bottom to the top to effect fine adjustment, resulting in difficult workability for the adjustment.

In contrast, when the delivery head is set near the middle point (m) between the lowermost point and the uppermost point, the drug liquid can be discharged approximately in the horizontal direction. Thus, monitoring, fine adjustment and the like of the coating state are easy.

The position of the delivery head is the same for both rotations of the adhesive sheet from the downward to the upward for 180° along the roll, and change of direction for an angle of less than 180° along the roll.

The posture of the delivery head (particularly, slot die), namely, an angle formed by the adhesive face with the discharge direction of the drug liquid is not limited. However, the angle θ1 measured at the downstream side of the delivery head (as shown in FIG. 3(a), the side where the adhesive sheet further traveled from the position of the delivery head) is preferably within the range of 80 degrees-110 degrees, more preferably within the range of 85 degrees-100 degrees.

When the angle θ1 formed by the adhesive face with a discharge direction of the drug liquid is less than 80 degrees, the drug liquid is excessively discharged toward the side of the adhesive sheet supplying part (upstream side), thus possibly causing dripping. Conversely, when the angle θ1 exceeds 110 degrees, the drug liquid is excessively discharged toward the direction of the downstream side, thus possibly making smooth application difficult to achieve.

In the embodiment of FIG. 1, a runway is so constituted as to allow the adhesive face 2a to move upward and downward in front of the outlet opening of the delivery head b1. In addition, the runway is so constituted as to allow the adhesive face 2a to change the moving direction by 90 degrees immediately after passing the outlet opening, and move horizontally with the adhesive face 2a as the top surface. In this way, an effect of downsizing of the whole manufacturing apparatus can be afforded.

Examples of a metering pump include syringe pump, gear pump, mohno pump, diaphragm pump, magnet pump and the like. From the aspects of high accuracy and the like, syringe pump is preferable, and gear pump and magnet pump are also preferable.

The metering accuracy of a pump is important as a factor having an influence on the content uniformity of drug liquid application.

Besides the kind of a metering pump, which is naturally important, a motor which drives the pump is also important. It is preferable to use a servo motor showing fewer changes in the number of revolution caused by disturbance.

Moreover, the moving speed of an adhesive face (traveling speed of an adhesive sheet) during application of the drug liquid and the accuracy thereof are also important. The application amount and application accuracy of the drug liquid can be roughly determined only by the ratio of the number of revolution and revolution accuracy and the traveling speed of the metering pump.

According to the production method of the present invention, since the absorption rate of a drug liquid is sufficiently fast, the accuracy of the rate of the number of revolution of a metering pump and line speed can directly be the application accuracy.

In addition, the factors influencing the content uniformity of the application of a drug liquid include pressure variation inside a drug liquid supply line and rheological characteristics of the drug liquid inside the die.

The pressure variation inside a drug liquid supply line is caused not only by the level of accuracy of the metering pump but also bubbles in the supply line. It is desirable to remove bubbles in a drug liquid supply line. As regards drug liquid supply, when the back-up roll R1 is set to make a horizontal rotation shaft, a drug liquid is desirably supplied mainly to the intersection of the horizontal plane passing the rotation shaft of the back-up roll R1 and the outer circumferential surface of the back-up roll R1, so that the bubbles can be removed easily. Moreover, a bubble trap apparatus (not shown) is desirably set in the line.

For the piping of a drug liquid supply line, a thin pipe is preferably used for easy removal of bubbles. The design of the pipe diameter varies depending on the supply amount of the drug liquid and cannot be determined generally. However, when the supply amount of the drug liquid is about 3 mL/min, the inner diameter of the piping is desirably 2-4 mm.

The material of the pipe may be any as long as it is not corroded by a drug liquid. Since the drug liquid may be a toxic substance, stainless is preferable. Even when the material of the pipe is corroded by a drug liquid, a coating having corrosion resistance to the drug liquid can be applied to the inside of the pipe. To confirm bubbles inside the pipe, a Teflon (registered trademark) pipe is also preferably used.

The adhesive face to be applied with a drug may have fine concaves and convexes of about ±50 μm. In addition, the adhesive face may be corrugated at the size of about ±50 μm depending on the dispersion in the thickness of the adhesive layer. When it exceeds ±50 μm, the application amount may become uneven.

In this apparatus, a drug liquid is directly used as an application liquid without dissolving in an auxiliary substance such as solvent and the like. Thus, the application liquid has low viscosity and the application line speed can be increased, which is extremely advantageous for improving the productivity and application accuracy.

The rheological characteristics of the application liquid in the die are also important for uniform application. Particularly, the uniformity in the width direction in a wide die depends on the inside structure of the die. Therefore, a die sufficiently designed for application of a drug liquid is preferably used.

A metal film or plastic film inert to a drug liquid is used as a shim and placed in a die, whereby the clearance of a discharging slot can be adjusted. As a shim, films having various thicknesses can be used.

Examples of the metal film inert to a drug liquid include stainless film, zinc foil film, titanium foil film and the like. Examples of the plastic film inert to a drug liquid include poly(ethylene terephthalate) film, Teflon (registered trade mark) film, cellulose acetate film, poly(vinyl chloride) film, polyethylene film, polypropylene film, polycarbonate film, polyamide film and the like. In consideration of the mechanical strength, moreover, most preferable materials of the shim are poly(ethylene terephthalate) film and stainless film. The thickness of the shim is influenced by the application thickness and application line speed. When the application thickness is 15-20 μm, 20 μm-100 μm is preferable.

As shown in FIG. 2(a), the clearance g between the tip face of the die and the adhesive face 2a is preferably 50 μm-1000 μm, particularly preferably 100 μm-800 μm. When the clearance is less than 50 μm, the dispersion in the amount of application due to the concaves and convexes on the surface of an adhesive layer may become remarkable, and when it exceeds 1000 μm, dripping may occur.

In consideration of the possibility of the application liquid being a toxic substance, moreover, it is desirable to provide a mechanism of automatically washing a die head, the inside of the die, piping and a tank. In consideration of volatilization from an exposed part of a drug liquid, moreover, it is desirable to set a safety cover on the exposed part of the drug liquid or install ventilation in the work room.

While a drug liquid is generally applied at room temperature, the temperature of the drug liquid to be applied is preferably kept at a given level, since changes in the room temperature vary the specific gravity of the drug liquid and also the amount applied. To keep the temperature of a drug liquid at a given level, an apparatus to maintain a constant temperature may be provided on a die, piping and a tank. When a drug liquid having a high temperature is applied, the penetration rate of the drug liquid into an adhesive layer increases, but the workers may be in a danger due to volatilization of the drug liquid. From the aspect of the safety of the workers, therefore, a drug liquid is preferably applied at a low temperature. The temperature of a drug liquid is preferably kept at 0-40° C., preferably 5-30° C., more preferably 10-25° C. The temperature change is preferably within ±2° C.

When nicotine is used as a drug liquid, a long-term preservation at high humidity in a place free of humidity control should preferably be avoided since nicotine has hygroscopicity. However, under extremely low humidity, nicotine may catch fire from static spark. Thus, it is desirably applied in a place under humidity control to a given relative humidity of 40-60%.

While the length of traveling section (C) for impregnation can vary depending on the kind of a drug liquid, it is preferably 70 mm-30000 mm, more preferably 1000 mm-20000 mm. When it is less than 70 mm, there is a fear that sufficient impregnation time cannot be secured, and when it exceeds 30000 mm, there is a fear that an apparatus scales up which is economically disadvantageous.

A specific example is further given where the drug liquid is nicotine. When nicotine is employed as a drug liquid, the length of traveling section (C) for impregnation is determined depending on the application amount (supply amount) per unit area of nicotine, penetration rate of nicotine in an adhesive layer and feeding speed of an adhesive sheet.

This length of the traveling section for impregnation is a minimum length. When a larger scale apparatus can be adopted, an adhesive sheet can continue to travel even after the determined section in such a manner that other solid will not contact an adhesive face, while considering the above-mentioned range.

The penetration rate of nicotine in an adhesive layer is preferably 0.3 $mg/cm^2 \cdot min$-6.7 $mg/cm^2 \cdot min$, more preferably 0.5 $mg/cm^2 \cdot min$-5.0 $mg/cm^2 \cdot min$, most preferably 0.8 $mg/cm^2 \cdot min$-3.8 $mg/cm^2 \cdot min$, (min=minute).

When it is not more than 6.7 $mg/cm^2 \cdot min$, the ratio of the liquid component in an adhesive layer is within a preferable range, and adhesive properties such as adhesive force, coagulation power, tack and the like are well balanced, which suppresses peeling and adhesive residue. When the penetration rate is not less than 0.3 $mg/cm^2 \cdot min$, a given amount of nicotine can efficiently soak in an adhesive layer during the application step.

From the aspects of treatment effect and economy, the application amount of nicotine per unit area is preferably about 1.6 ($mg/cm^2$) for a preparation having the lowest concentration and about 5.5 ($mg/cm^2$) for a preparation having the highest concentration.

As mentioned above, the penetration rate of nicotine in an adhesive layer is preferably about 0.3-6.7 ($mg/cm^2 \cdot min$) (an adhesive and a liquid component are so mixed as to achieve such penetration rate).

At this time, the time necessary for penetration of all the nicotine applied onto an adhesive face of an adhesive layer is preferably about 15 sec-1100 sec, more preferably 20-660 sec, most preferably 25-410 sec (sec=second). At least this amount of time is secured by a traveling section for impregnation.

On the other hand, from the aspects of the strength of an adhesive sheet and stable application, the line traveling speed of an adhesive sheet is preferably 0.064 mm/sec-2000 mm/sec, more preferably 0.64 mm/sec-200 mm/sec, most preferably 4.7 mm/sec-0.27 mm/sec.

When the length of the traveling section for impregnation is shorter than the aforementioned range, a drug liquid remaining as a liquid on an adhesive face contacts other members and uniform coating cannot be realized. When the length of the traveling section for impregnation is excessively longer than the aforementioned range, defects also unpreferably appear such as the whole apparatus that has become larger by the corresponding extent and the like.

During application of a drug liquid, as mentioned earlier, since the application precision depends solely on the ratio of the number of rotation of a metering pump and the feeding rate of an adhesive sheet in the runway, a mechanism for controlling electric signals between the metering pump and the line speed or for a feed back of the number of rotation may be formed, which is desirably designed to automatically increase the rotation speed of the pump at a given rate in response to an increased line speed.

Furthermore, a release liner laminating part (E) for adhering a band-like release liner to a drug-impregnated adhesive layer of a traveling adhesive sheet is formed after the traveling section for impregnation in the runway. In the embodiment of FIG. 1, a release liner 5 supplied synchronously from a release liner supplying part (D) is adhered to an adhesive sheet 3 during passage of the adhesive sheet between two rolls R2 and R3, which are the main parts of a release liner laminating part (E), and delivered as a final product to a product receipt part (F).

As regards the constitution of the apparatus for supplying a release liner in the release liner supplying part (D), and the mechanism and technique per se for synchronously laminating a release liner on an adhesive face in the release liner laminating part (E), conventionally-known production techniques for adhesive sheets can be utilized.

As the release liner, a liner generally used for transdermal absorption preparations can be used. For example, a poly(ethylene terephthalate) film release treated with a known release treatment agent (e.g., polymer containing long chain alkyl group, silicone polymer, fluorine polymer, etc.) and the like can be mentioned. The thickness of the release liner is generally 25-500 μm.

In the constitution of FIG. 1, the final part of the runway is a product receipt part (F). The product receipt part (F) may be a part for winding, as a roll, a transdermal absorption or preparation (band-like product) completed as a product by imparting a release liner 5, or a reeling apparatus that simultaneously works outside the apparatus or a simple outlet port for feeding out a transdermal absorption preparation to the next processing apparatus.

The shape and size of a transdermal absorption preparation produced by the apparatus are not particularly limited, and may be any shape and size according to the adhesion site and the like. The shape may be, for example, a tape, a sheet and the like. The size of the preparation is, for example, 5-30 cm$^2$.

The transdermal absorption preparation to be produced by the method of the present invention using nicotine as a drug liquid can be used for a drug supplemental therapy in line with a stop-smoking program conventionally practiced or to be practiced in the future, which aims at suppressing habitual smoking of smokers (particularly, those wishing to quit smoking) and the like.

While the dose of the transdermal absorption preparation produced by the method of the present invention varies depending on the kind of the drug, age and body weight of the patients, severity of the disease and the like, a transdermal absorption preparation containing 5-120 mg of a drug is generally applied to 5-30 cm$^2$ of the skin of an adult at a frequency of once per 0.5-2 days.

EXAMPLE

Preparation of an Adhesive Solution

Under nitrogen atmosphere, 2-ethylhexyl acrylate (72 parts), N-vinyl-2-pyrrolidone (25 parts), acrylic acid (3 parts) and ethyl acetate (200 parts) were charged in a flask, azobisisobutyronitrile (0.3 part) was added as a polymerization initiator, and polymerization was started.

The inner bath temperature was controlled to 58-62° C. by controlling the stirring rate and outer bath temperature and dropwise addition of ethyl acetate. A polymerization reaction was performed, and an adhesive solution was prepared.
(Formation of an Adhesive Layer on a Release Liner)

The above-mentioned adhesive solution in an amount corresponding to an adhesive solid content (59.79 parts) was measured in a reaction vessel. Isopropyl palmitate (10 parts) was added, and then COCONAD MT (30 parts, manufactured by KAO CORPORATION, tri(caprylic acid/capric acid)glyceride) and aluminum acetylacetonate (0.35% relative to the adhesive, manufactured by SIGMA-ALDRICH Corporation) were added to the adhesive solution, and the mixture was thoroughly stirred.

The obtained solution was applied to one surface of a poly(ethylene terephthalate) release liner, which surface had been release treated, to a thickness after drying of 70 μm. After drying at 70° C. for 2 min, the surface was further dried at 90° C. for 2 min to form an adhesive layer.
(Adhesion of a Support)

A 2 μm-thick poly(ethylene terephthalate) film was laminated on a polyester non-woven fabric (fabric weight 12 g/m$^2$) extrusion forming to give a support. The non-woven fabric side of the support was adhered to the adhesive face of the above-mentioned adhesive layer to give a laminate. Thereafter, the laminate was tightly sealed and left standing at 60° C. for 48 hr. The adhesive layer was crosslinked to give a crosslinked adhesive layer to give a placebo adhesive sheet without a drug in the adhesive layer.

As a manufacturing apparatus of a transdermal absorption preparation, an apparatus shown in FIG. 1 was produced.

A placebo adhesive sheet 3 free of a release liner was sent out into a runway from an adhesive sheet supplying part (A) while detaching a first release liner of the placebo adhesive sheet to expose the adhesive face.

A die coater was provided as an application apparatus on a drug liquid application part (B). Using the die coater, free form nicotine without forming a salt was applied to the adhesive face of the crosslinked adhesive layer. A die coater equipped with a 35 μm-thick poly(ethylene terephthalate) shim was set at a horizontal position, and a delivery head of the die was set perpendicularly to the crosslinked adhesive layer.

To give a sheet before punching out a nicotine transdermal absorption preparation having a nicotine content of 1.8 mg/cm$^2$, the clearance between the die tip and the crosslinked adhesive layer was set to 500 μm, the line speed of the placebo adhesive sheet that passes the application part was set to 2 m/min, the supply amount of free form nicotine was set to 3.6 mL/min and the application width was set to 10 cm. Under these conditions, nicotine was applied.

At this point, immediately after discharge of nicotine on the surface of the adhesive sheet from the die as shown in FIG. 2(b), nicotine was present in a droplet state on the adhesive face of the crosslinked adhesive layer. However, nicotine uniformly soaked into the crosslinked adhesive layer while the adhesive sheet ran through the traveling section (C) for impregnation of the runway. Thereafter, the release treated surface of the release treated poly(ethylene terephthalate) release liner was adhered to the surface applied with nicotine to give a raw sheet of nicotine transdermal absorption preparation with a width of 10 cm and a length of 78 m.

Square pieces (5 cm$^2$) were punched out from the raw sheet at every 2 m starting from 0.5 m from the beginning of the application, with the center of the pieces being 2 cm from the end of one edge of the raw sheet in the longitudinal direction and 2 cm from the end of the other edge to give transdermal absorption preparations.

The nicotine content of each transdermal absorption preparation was determined by HPLC. The results are shown in Table 1.

TABLE 1

| m | one edge | the other edge |
|---|---|---|
| 0.5 | 1.80 | 1.78 |
| 2.5 | 1.81 | 1.80 |

TABLE 1-continued

| m | one edge | the other edge |
|---|---|---|
| 4.5 | 1.82 | 1.83 |
| 6.5 | 1.83 | 1.82 |
| 8.5 | 1.84 | 1.82 |
| 10.5 | 1.81 | 1.82 |
| 12.5 | 1.82 | 1.81 |
| 14.5 | 1.83 | 1.83 |
| 16.5 | 1.84 | 1.83 |
| 18.5 | 1.83 | 1.83 |
| 20.5 | 1.84 | 1.84 |
| 22.5 | 1.82 | 1.83 |
| 24.5 | 1.84 | 1.84 |
| 26.5 | 1.82 | 1.82 |
| 28.5 | 1.82 | 1.83 |
| 30.5 | 1.83 | 1.83 |
| 32.5 | 1.83 | 1.82 |
| 34.5 | 1.82 | 1.83 |
| 36.5 | 1.83 | 1.83 |
| 38.5 | 1.84 | 1.81 |
| 40.5 | 1.81 | 1.85 |
| 42.5 | 1.83 | 1.82 |
| 44.5 | 1.82 | 1.82 |
| 46.5 | 1.82 | 1.83 |
| 48.5 | 1.79 | 1.79 |
| 50.5 | 1.79 | 1.80 |
| 52.5 | 1.83 | 1.80 |
| 54.5 | 1.80 | 1.79 |
| 56.5 | 1.80 | 1.80 |
| 58.5 | 1.80 | 1.80 |
| 60.5 | 1.80 | 1.79 |
| 62.5 | 1.79 | 1.80 |
| 64.5 | 1.79 | 1.79 |
| 66.5 | 1.80 | 1.79 |
| 68.5 | 1.78 | 1.79 |
| 70.5 | 1.78 | 1.78 |
| 72.5 | 1.78 | 1.78 |
| 74.5 | 1.79 | 1.78 |
| 76.5 | 1.79 | 1.78 |
| 78.5 | 1.78 | 1.78 |
| average | 1.81 | 1.81 |
| standard deviation | 0.02 | 0.02 |
| relative standard deviation % | 1.10 | 1.10 |
| average | 1.81 | |
| standard deviation | 0.02 | |
| relative standard deviation % | 1.10 | |

As is clear from Table 1 above, the nicotine content on both edges of the raw sheet of one transdermal absorption preparation was average (A) (1.81 mg/cm$^2$), standard deviation (SD) (0.02 mg/cm$^2$) and relative standard deviation % (CV %, (SD)÷A×100) (1.10%), and it was found that the transdermal absorption preparation uniformly contained nicotine.

According to the manufacturing apparatus of the present invention, a transdermal absorption preparation wherein a drug liquid is directly applied to an adhesive layer, which reduces a loss caused by decomposition due to heat history, scattering and the like, causes less physical irritation to the skin on detachment, and affords good feeling during adhesion, can be efficiently produced.

This application is based on a patent application No. 2006-343395 filed in Japan, the contents of which are incorporated in full herein by this reference.

The invention claimed is:

1. A method for manufacturing a nicotine-containing transdermal absorption preparation, comprising:
providing an adhesive sheet supplying part that feeds out a first adhesive sheet into a runway at a traveling speed, the adhesive sheet having an adhesive face and at least an adhesive layer comprising an adhesive and a liquid component compatible with the adhesive, and the traveling speed of the adhesive sheet on the runway being 0.064 mm/second to 2000 mm/second, the adhesive being an acrylic adhesive, the liquid component being an organic liquid component comprising at least one of fatty acid alkyl esters and glycerol fatty acid esters, and a mixing ratio of the adhesive and the liquid component in the adhesive layer being 1:0.25-1:1.8 in a weight ratio,
providing a drug liquid application part that applies a given amount of a drug liquid, the drug liquid being a nicotine and/or a nicotine solution, to the adhesive face of the traveling adhesive sheet,
wherein the combination of the drug liquid, an adhesive and the liquid component is determined so as:
to impregnate the adhesive layer with the drug liquid, and
to achieve a contact angle of the drug liquid with the adhesive face of 20 degrees-60 degrees,
wherein the drug liquid application part discharges a given amount of a drug liquid on the adhesive face from a delivery head arranged in close proximity to the adhesive face,
providing a traveling section for impregnation positioned along the runway after the drug liquid application part, the traveling section enabling the adhesive sheet to run for a period necessary for the applied drug liquid to soak into the adhesive layer,
wherein the length of the traveling section for impregnation is 70 mm to 30000 mm, and the length is determined based on the traveling speed of the adhesive sheet so the adhesive sheet runs along the traveling section for impregnation for 15 seconds to 1100 seconds, which is the time necessary for penetration of all the drug liquid applied, and
wherein the runway comprises a roll in contact with the back face of the adhesive sheet, the roll having a horizontal rotation shaft, the runway is arranged in such a manner that the adhesive face of the adhesive sheet rotates from a downward position to an upward position for 180 degrees along the roll, and the delivery head is positioned within the range of −90 degrees to +90 degrees about the middle point between the lowermost point and the uppermost point of the roll.

2. The method of claim 1, wherein the shape of an outlet opening of the delivery head is a slot covering not less than half of the whole width of the adhesive face so that the drug liquid is discharged over the region covering not less than half of the whole width of the adhesive face.

3. The method of claim 1, wherein the delivery head is directed so as to form an angle between the adhesive face and the drug liquid discharge direction of 80-110 degrees as measured downstream of the delivery head.

4. The method of claim 1, further providing a release liner laminating part that adheres a release liner to the adhesive face of the traveling adhesive sheet arranged in a position after the traveling section for impregnation in the runway.

5. The method of claim 1, further providing a second adhesive sheet supplying part that supplies a second adhesive sheet arranged in a position after the traveling section for impregnation in the runway, the second adhesive sheet supplying part adhering an adhesive face of the second adhesive sheet to the adhesive face of the first adhesive sheet.

6. The method of claim 5, wherein each of the first adhesive sheet and the second adhesives sheet is band.

7. The method of claim 1, wherein the first adhesive sheet is a band.

8. The method of claim 1, wherein the drug liquid has a low viscosity.

9. The method of claim 1, wherein the traveling section enables the applied drug liquid to soak into the adhesive face when the adhesive face is facing in a direction opposite the direction of gravity.

10. The method of claim 1, wherein the adhesive face includes convexes and concaves or is corrugated.

* * * * *